United States Patent
Sano (10) Patent No.: US 8,439,889 B2
(45) Date of Patent: May 14, 2013

(54) BLOOD BAG SYSTEM AND BLOOD TREATING METHOD

(75) Inventor: Shinya Sano, Ashigarakami-gun (JP)

(73) Assignee: Terumo Kabushiki Kaisha, Shibuya-Ku, Tokyo (JP)

(*) Notice: Subject to any disclaimer, the term of this patent is extended or adjusted under 35 U.S.C. 154(b) by 24 days.

(21) Appl. No.: 13/132,780

(22) PCT Filed: Nov. 18, 2009

(86) PCT No.: PCT/JP2009/069531
§ 371 (c)(1),
(2), (4) Date: Jun. 3, 2011

(87) PCT Pub. No.: WO2010/064538
PCT Pub. Date: Jun. 10, 2010

(65) Prior Publication Data
US 2011/0238030 A1   Sep. 29, 2011

(30) Foreign Application Priority Data
Dec. 3, 2008 (JP) .................... 2008-308462

(51) Int. Cl.
*A61B 19/00* (2006.01)
(52) U.S. Cl.
USPC ........... 604/403; 210/749; 210/767; 210/645; 604/408
(58) Field of Classification Search ............ 604/410, 604/6.15, 6.19; 210/744
See application file for complete search history.

(56) References Cited

U.S. PATENT DOCUMENTS

| 4,963,260 A | * | 10/1990 | Naoi et al. | 210/446 |
| 4,985,153 A | * | 1/1991 | Kuroda et al. | 210/782 |
| 2003/0106861 A1 | | 6/2003 | Gibbs et al. | |

FOREIGN PATENT DOCUMENTS

| JP | 60-193468 A | | 10/1985 |
| JP | 1-320064 A | | 12/1989 |
| JP | 06246985 A | * | 9/1994 |
| JP | 2004-166748 A | | 6/2004 |
| JP | 2005-802 A | | 1/2005 |
| JP | 2005-512623 A | | 5/2005 |
| JP | 2006-246985 A | | 9/2006 |

OTHER PUBLICATIONS

International Search Report (PCT/ISA/210) issued on Feb. 23, 2010, by Japanese Patent Office as the International Searching Authority for International Application No. PCT/JP2009/069531.

* cited by examiner

*Primary Examiner* — Leslie Deak
*Assistant Examiner* — Jordan B Bailey
(74) *Attorney, Agent, or Firm* — Buchanan Ingersoll & Rooney PC (57) ABSTRACT

The blood bag system includes: a blood treating filter for treating a blood; a first bag for containing therein a blood to be supplied to the blood treating filter; a second bag for containing therein the blood treated by the blood treating filter; storage solution supply which supplies a blood component storage solution to the blood treating filter; a third bag into which a blood remaining in the blood treating filter replaced by the blood component storage solution is transferred and in which the recovered blood is temporarily contained; and a fourth bag to which a blood component separated from the treated blood contained in the second bag is transferred and in which the transferred blood component is contained.

8 Claims, 11 Drawing Sheets

FOURTH STEP

BLOOD BAG SYSTEM AND BLOOD TREATING METHOD

TECHNICAL FIELD

The present invention relates to a blood bag system and a blood treating method for preparing a blood component preparation to be used for blood transfusion, such as concentrated red blood cell (hereinafter referred to as CRC), platelet concentrated (hereinafter referred to as PC), platelet poor plasma (hereinafter referred to as PPP), platelet rich plasma (hereinafter referred to as PRP), or the like.

BACKGROUND ART

In the past, blood component preparations have been prepared by removing white blood cells from a blood collected from a donor, and subjecting the blood deprived of the white blood cells to centrifugal separation. For instance, Japanese Patent Laid-open No. 2004-166748 describes a recovery method and a recovery apparatus wherein a blood is made to flow via a blood inlet port into a white blood cell removing filter by use of a blood feeding means so as to catch white blood cells by the white blood cell removing filter, and the blood remaining in the white blood cell removing filter is recovered by a recovery solution, which is a physiological solution.

However, in the recovery method and recovery apparatus described in Patent Document 1, both the blood deprived of the white blood cells and a recovery solution with which the blood remaining in the white blood cell removing filter has been recovered are contained into a recovery bag, and both of them are centrifugally separated, to prepare blood component preparations (CRC, PC and PPP). Therefore, the thus prepared PPP contains the recovery solution (physiological solution) therein, resulting in the problem that the PPP concentration is lowered. In addition, in the CRC and PC thus prepared, the physiological solution is not enough preservative to effect on a lowering in the function of the red blood cells or the platelets. Therefore, there is also the problem that a blood component storage solution (a red blood cell storage solution or a platelet storage solution) has to be newly added.

In view of the foregoing, the present invention has been devised for solving the just-mentioned problems. Accordingly, it is an object of the present invention to provide a blood bag system and a blood treating method wherein a lowering in the concentrations of blood component preparations prepared is obviated, there is no need for a new addition of a blood component storage solution, and it is possible to contrive enhancement of recovery factors of the blood component preparations.

TECHNICAL SOLUTION

In order to solve the above problems, according to a first embodiment of a blood bag system pertaining to the present invention, there is provided a blood bag system including: a blood treating filter for treating a blood; a first bag for containing therein a blood to be supplied to the blood treating filter; a second bag for containing therein the blood treated by the blood treating filter; storage solution supply means for supplying a blood component storage solution to the blood treating filter; a third bag into which a blood remaining in the blood treating filter replaced by the blood component storage solution is transferred and in which the recovered blood is temporarily contained; and a fourth bag to which a blood component separated from the treated blood contained in the second bag is transferred and in which the thus transferred blood component is contained.

In addition, the blood bag system is characterized in that the blood treating filter is a white blood cell and platelet removing filter for removing white blood cells and platelets from whole blood, the first bag is a blood collecting bag for collecting whole blood, the second bag is a red blood cell storing bag, the blood component storage solution is a red blood cell storage solution, and the fourth bag is a plasma storing bag. Further, the blood bag system is characterized in that the storage solution supply means is a bag-shaped container containing the blood component storage solution therein which container is preliminarily connected, or the bag-shaped container which is connected in a sterile manner before use.

According to the above-mentioned configuration, the provision of the storage solution supply means for supplying the blood component storage solution to the blood treating filter ensures that the blood remaining in the blood treating filter can be recovered with the blood component storage solution, and can be used together with the treated blood for preparing blood component preparations. Consequently, the amount of blood which can be used for preparing the blood component preparations (specifically, CRC and PPP) is increased.

Besides, the provision of the third bag for containing the recovered blood therein ensures that the blood component storage solution is not mixed into the treated blood in the second bag which is to be used for preparing a blood preparation. Therefore, the concentration of the blood component preparation (specifically, PPP) prepared in the second bag is not lowered by the blood component storage solution.

Further, since the blood component storage solution is preliminarily provided as a component (storage solution supply means) of the blood bag system, it can be used to prevent a lowering in the function of the blood component preparation (specifically, CRC).

A second embodiment of the blood bag system according to the present invention further includes, in addition to the first embodiment, a fifth bag to which a blood component separated from the recovered blood contained in the third bag is transferred and in which the thus transferred blood component is temporarily contained; and a sixth bag to which a blood component separated further from the blood component transferred into the fourth bag is transferred and in which the thus transferred blood component is temporarily contained.

In addition, the blood bag system is characterized in that the blood treating filter is a white blood cell removing filter for removing white blood cells from whole blood, the first bag is a blood collecting bag for collecting whole blood, the second bag is a red blood cell storing bag, the blood component storage solution is a platelet storage solution, the fourth bag is a platelet storing bag, and the sixth bag is a plasma storing bag. Besides, the blood bag system is characterized in that the sixth bag contains a red blood cell storage solution therein before containing the blood component. In addition, the blood bag system is characterized in that the third bag and the fifth bag are united together through a diaphragm. Furthermore, the blood bag system is characterized in that the storage solution supply means is a bag-shaped container containing the blood component storage solution therein which container is preliminarily connected, or the bag-shaped container which is connected in a sterile manner before use.

According to the above-mentioned configuration, the provision of the storage solution supply means for supplying the blood component storage solution to the blood treating filter ensures that the blood remaining in the blood treating filter can be recovered with the blood component storage solution, and can be used together with the treated blood for preparing blood component preparations. Consequently, the amount of blood which can be used for preparing the blood component preparations (specifically, CRC, PPP and PC) is increased.

Besides, the provision of the third bag for containing the recovered blood therein ensures that the blood component storage solution supplied from the storage solution supply means is not mixed into the treated blood in the second bag which is to be used for preparing a blood preparation. Therefore, the concentration of the blood component (specifically, PRP) separated in the second bag is not lowered by the blood component storage solution. As a result, the concentration of the blood component preparation (specifically, PPP) prepared from PRP in the fourth bag is not also lowered by the blood component storage solution.

In addition, since the blood component storage solution is preliminarily provided as components (the storage solution supply means and the sixth bag) of the blood bag system, it can be used to prevent a lowering in the function of the blood component preparation (specifically, CRC and PC).

Furthermore, the provision of the fifth bag for containing the blood component separated from the recovered blood ensures that the blood component storage solution contained in the recovered blood can be used to prevent a lowering in the function of the blood component preparation (specifically, PC), and that it is unnecessitated to use part of a blood component preparation (specifically, PPP) for preventing a lowering in the function of another blood component preparation (specifically, PC), as in the related art.

A first method of a blood treating method according to the present invention is a method of treating a blood by use of the blood bag system of the first embodiment, including: a first step of supplying the blood contained in the first bag into the blood treating filter, containing the blood treated by the blood treating filter into the second bag, thereafter supplying the blood component storage solution from the storage solution supply means into the blood treating filter so as to recover the blood remaining in the blood treating filter, and containing the recovered blood into the third bag; a second step of centrifuging the second bag so as to separate the treated blood contained in the second bag into two blood components; and a third step of transferring, in such a manner as to leave one of the blood components in the second bag, the other blood component to the fourth bag, and thereafter transferring the recovered blood contained in the third bag to the second bag so as to mix the recovered blood with the one blood component.

According to the above-mentioned procedure, the first step of supplying the blood component storage solution from the storage solution supply means into the blood treating filter so as to contain the resulting liquid into the third bag as the recovered blood is included, whereby the blood remaining in the blood treating filter can be recovered by the blood component storage solution, and can be used together with the treated blood to prepare blood component preparations. Therefore, the amount of blood which can be used for preparing the blood component preparations (specifically, CRC and PPP) is increased. In addition, the blood component storage solution (recovered blood) is not mixed into the treated blood in the second bag which is to be used to prepare the blood component preparations, so that the concentration of the blood component preparation (specifically, PPP) prepared through the separation in the second step and the transfer to the fourth bag in the third step is not lowered by the blood component storage solution.

In addition, since the third step of mixing the recovered blood (specifically, the blood component storage solution and CRC) in the third bag into the blood component (specifically, CRC) in the second bag which has been separated in the second step is included, the blood component storage solution can be used to prevent a lowering in the function of the blood component preparation (specifically, CRC).

A second method of the blood treating method according to the present invention is a method of treating a blood by use of the blood bag system of the second embodiment, including: a first step of supplying the blood contained in the first bag into the blood treating filter, containing the blood treated by the blood treating filter into the second bag, thereafter supplying the blood component storage solution from the storage solution supply means into the blood treating filter so as to recover the blood remaining in the blood treating filter, and containing the recovered blood into the third bag; a second step of centrifuging the second bag and the third bag so as to separate each of the treated blood contained in the second bag and the recovered blood contained in the third bag into two blood components; a third step of transferring, in such a manner as to leave one of the blood components in the second bag, the other blood component to the fourth bag, and transferring, in such a manner as to leave one of the blood components in the third bag, the other blood component to the fifth bag, followed by transferring the one blood component in the third bag to the second bag so as to mix the thus transferred one blood component with the one blood component in the second bag; a fourth step of centrifuging the fourth bag so as to further separate the other blood component contained in the fourth, bag into two blood components; and a fifth step of transferring, in such a manner as to leave one of the blood components in the fourth bag, the other blood component to the sixth bag, and thereafter transferring the other blood component in the fifth bag to the fourth bag so as to mix the thus transferred other blood component with the one blood component in the fourth bag.

According to the above-mentioned procedure, the first step of supplying the blood component storage solution from the storage solution supply means into the blood treating filter so as to contain the resulting liquid into the third bag as the recovered blood is included, whereby the blood remaining in the blood treating filter can be recovered by the blood component storage solution, and can be used together with the treated blood to prepare blood component preparations. Therefore, the amount of blood which can be used to prepare the blood component preparations (specifically, CRC, PPP and PC) is increased. In addition, the blood component storage solution (recovered blood) is not mixed into the treated blood in the second bag which is to be used to prepare the blood component preparations, so that the concentration of the blood component preparation (specifically, PRP) separated in the second step is not lowered by the blood component storage solution. As a result, the concentration of the blood component preparation (specifically, PPP) prepared in the sixth bag in the fifth step, after the transfer of the PRP to the fourth bag in the third step and the separation in the fourth step, is not also lowered by the blood component storage solution.

Besides, the third step of transferring the blood component (specifically, PRP) in the second bag which has been separated in the second step to the fourth bag and transferring the blood component (specifically, the blood component storage solution and PC) in the third bag to the fifth bag, the fourth step of separating the blood component (specifically, PRP) in the fourth bag into two (specifically, PPP and PC), and the fifth step of mixing the blood component (specifically, the blood component storage solution and PC) in the fifth bag into the blood component (specifically, PC) in the fourth bag, are included. This ensures that the blood component storage solution can be used to prevent a lowering in the function of the blood component preparation (specifically, PC), and it is unnecessitated to use the blood component (specifically, PPP) in the fourth bag to prevent a lowering in the function of the blood component (specifically, PC) in the fourth bag.

ADVANTAGEOUS EFFECTS

According to the blood bag system and the blood treating method pertaining to the present invention, the blood component storage solution (recovered blood) is not mixed into the treated blood, so that the blood component preparation (specifically, PPP) is not diluted with the blood component storage solution without the result of a lowering in the concentration thereof. Besides, since the blood component storage solution is used for recovery of the blood remaining in the blood treating filter, it is unnecessary to newly add a blood component storage solution. Further, since the treated blood and the recovered blood are used to prepare blood component preparations, the amount of blood which can be used to prepare the blood component preparations, so that it is made possible to contrive enhancement of recovery factors of the blood component preparations (specifically, CRC, PPP and PC). Incidentally, the blood component storage solution is used to prevent a lowering in the function of PC, and the use of part of PPP for this purpose as in the related art is obviated. Therefore, it is possible to contrive further enhancement of the recovery factor of PPP; in addition, in relation to PC, alleviation of transfusion side-effects arising from PPP can be expected.

MODE FOR CARRYING OUT THE INVENTION

<Blood Bag System>

Figure 1:
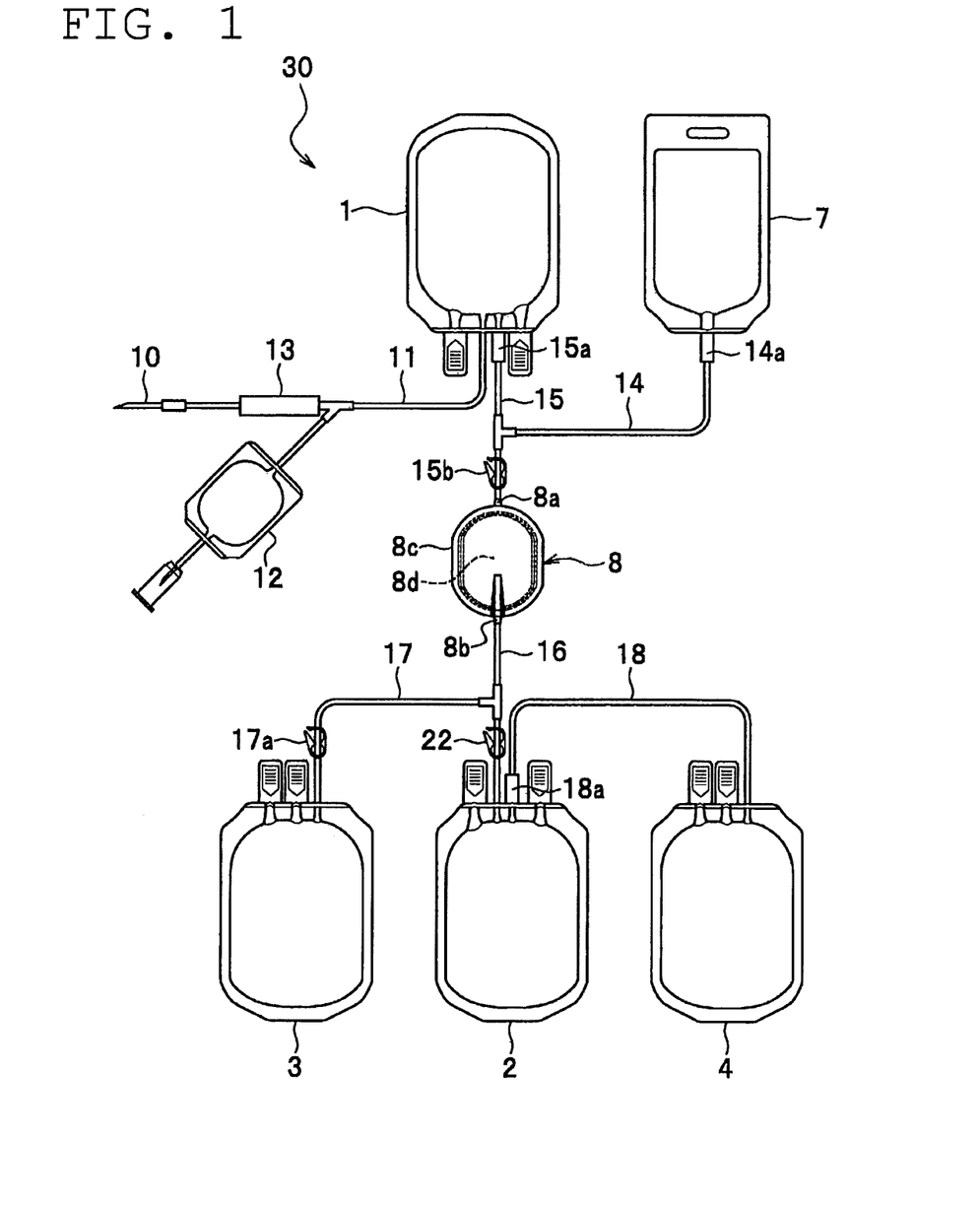
FIG. 1 is an appearance view showing the configuration of a first embodiment of a blood bag system according to the present invention.
Figure 2:
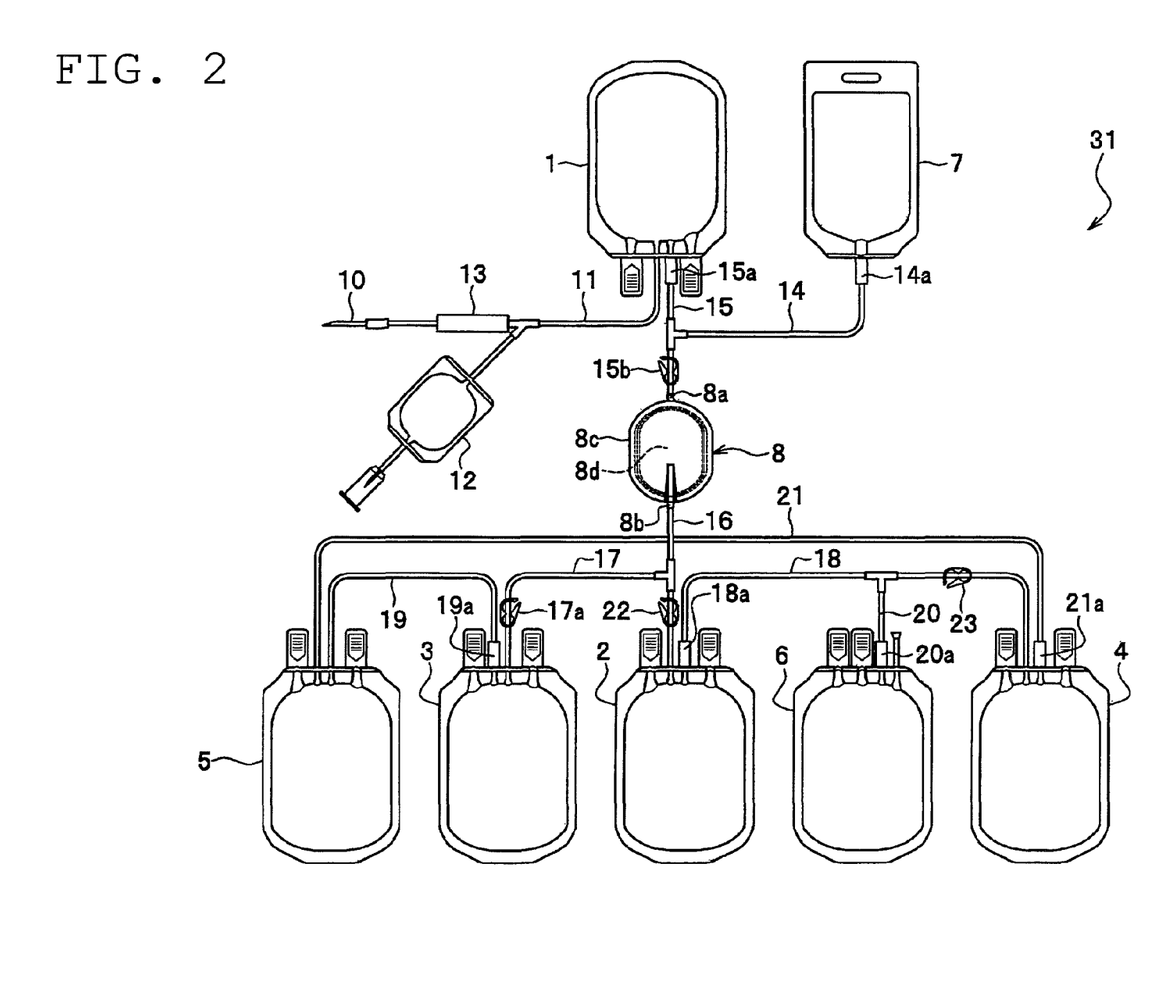
FIG. 2 is an appearance view showing the configuration of a second embodiment of the blood bag system according to the present invention.
Figure 3:
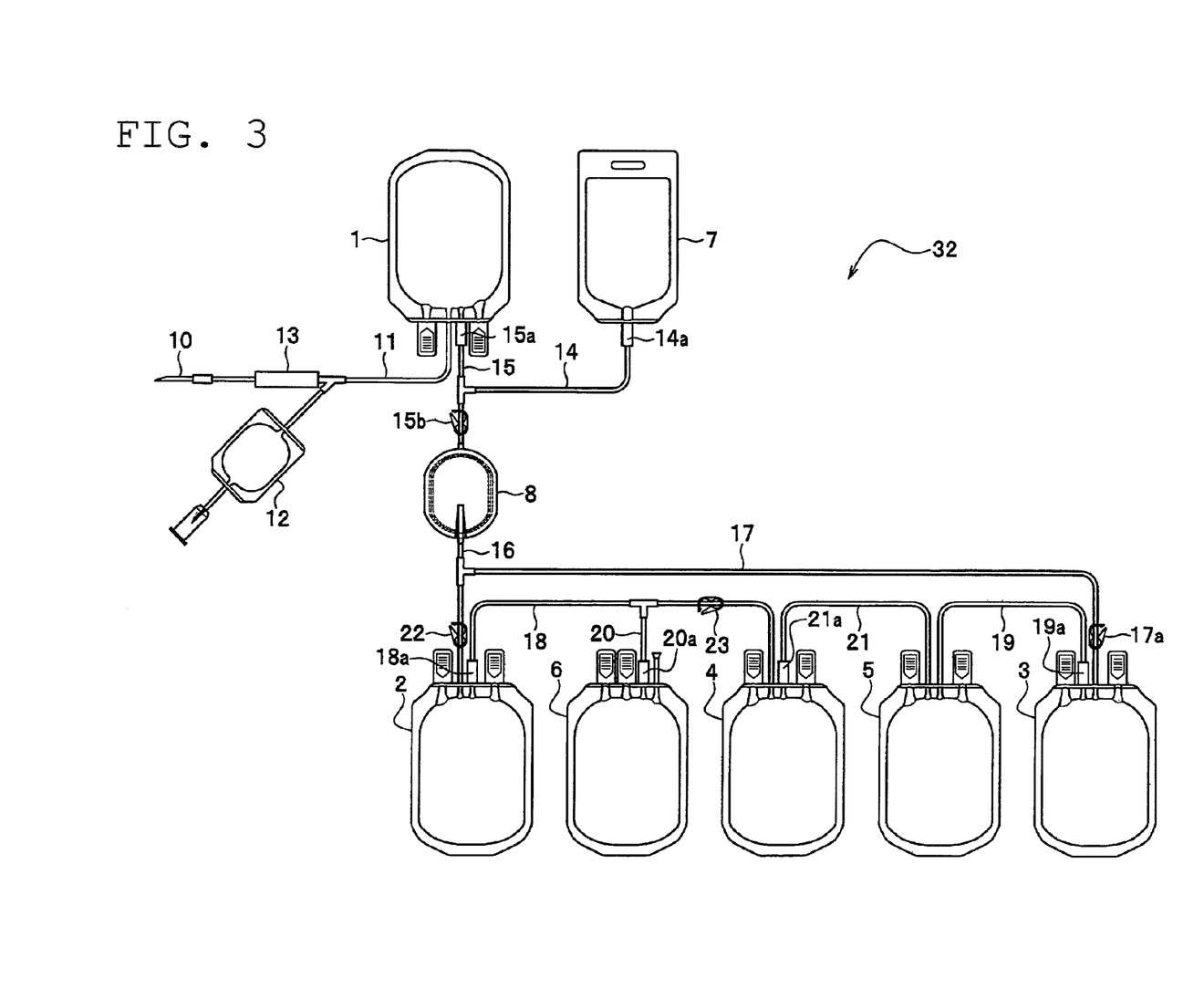
FIG. 3 is an appearance view showing the configuration of another embodiment of the blood bag system of FIG. 2.
Figure 4:
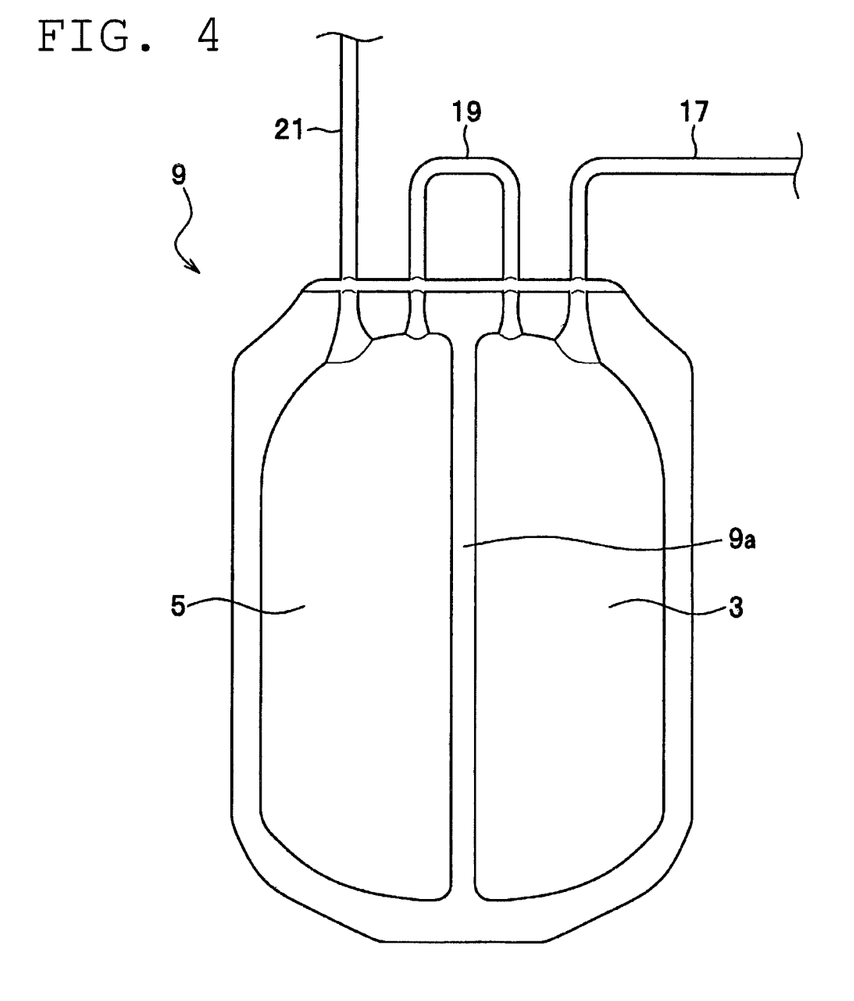
FIG. 4 is an appearance view showing the configuration of another embodiment of a third bag and a fifth bag in the blood bag system according to the present invention.

Embodiments of the blood bag system according to the present invention will be described in detail, while referring to the drawings. FIG. 1 is an appearance view showing the configuration of a first embodiment of the blood bag system, FIG. 2 is an appearance view showing the configuration of a second embodiment of the blood bag system, FIG. 3 is an appearance view showing the configuration of another embodiment of the blood bag system shown in FIG. 2, and FIG. 4 is an appearance view showing the configuration of another embodiments of a third bag and a fifth bag.

The first embodiment of the blood bag system will be described.

As shown in FIG. 1, a blood bag system 30 has a first bag 1 and a storage solution supply means 7 on the upstream side of a blood treating filter 8, and has a second bag 2, a third bag 3 and a fourth bag 4 on the downstream side of the blood treating filter 8.

In the blood bag system 30, the first bag 1 is connected to an inflow port 8a of the blood treating filter 8 through a tube 15, and the storage solution supply means 7 is connected to the inflow port 8a of the blood treating filter 8 through a tube 14 branched from the tube 15. In addition, the second bag 2 is connected to an outflow port 8b of the blood treating filter 8 through a tube 16, whereas the third bag 3 is connected to the outflow port 8b of the blood treating filter 8 through a tube 17 branched from the tube 16, and the fourth bag 4 is connected to the second bag 2 through a tube 18. Now, configurations of these members will be described below.

(Blood Treating Filter)

The blood treating filter 8 is a filter for performing a treatment of removing a predetermined blood component from a blood supplied from the first bag 1 described later, and, in the blood bag system 30, it is preferably a filter for performing a treatment of removing white blood cells and platelets. In addition, the blood treating filter 8 has a configuration in which a filter section 8d composed of a porous film formed from polyurethane or the like or a non-woven fabric formed from polyethylene terephthalate or the like is disposed in a housing 8c which has the inflow port 8a and the outflow port 8b and which is formed from polyvinyl chloride or the like. Further, the filter section 8d preferably has a predetermined surface zeta potential. In the case where the filter section 8d is composed of the porous film, the surface zeta potential is preferably +16 to +18 mV; where the filter section 8d is composed of the non-woven fabric, the surface zeta potential is preferably −20 to −30 mV.

(First Bag)

The first bag 1, which is for supplying a blood contained therein to the blood treating filter 8, is a bag-shaped container produced by laying sheets of a flexible resin such a polyvinyl chloride on each other and welding peripheral portions of the sheets to obtain a bag-shaped body. In addition, the internal volume of the first bag 1 is appropriately selected according to the amount of blood to be contained therein, and is 200 to 1000 ml. Further, the first bag 1 preferably is preliminarily filled with an anticoagulant such as ACD solution, CPD solution, etc. Conventionally, the first bag 1 has been filled with a predetermined amount of air so as to reduce the amount of blood (remaining blood) which will remain in the blood treating filter 8. However, if air is present inside the blood treating filter 8, recovery of the remaining blood by a blood component storage solution to be described later would be blocked, so that recovery factor tends to be lowered. Therefore, it is preferable for the amount of air in the first bag 1 to be as small as possible.

The first bag 1 is connected with a blood collecting means including a blood collecting needle 10 and a blood collecting tube 11, for supplying a blood into the inside of the first bag 1. In addition, the blood collecting means may have an initial flow collecting implement (testing blood bag) 12 branched from the blood collecting tube 11 and connected, and a mis-stick preventive implement 13 for preventing mis-stick with the blood collecting needle 10. Besides, the first bag 1 is connected with the tube 15 for supplying the contained blood to the blood treating filter 8, and the tube 15 is provided with a flow path plugging member 15*a* on the first bag 1 side and a tube clamp 15*b* on the blood filter 8 side. Incidentally, the flow path plugging member 15*a* has a cover tube, and a tube member having a solid tip portion contained therein so as to plug up a flow path, and is so configured that the flow path inside the cover tube is opened by breakage of the solid tip portion of the tube member.

(Storage Solution Supply Means)

The storage solution supply means 7, which is for supplying a blood component storage solution to the blood treating filter 8, is a bag-shaped container the same as or similar to the first bag 1, and is formed from polyvinyl chloride sheets, ethylene-vinyl acetate sheets or the like. However, the storage solution supply means 7 is not limited to a bag-shaped container, insofar as it can supply a blood component storage solution to the blood treating filter 8. In addition, the storage solution supply means 7 is connected with the tube 14 through which to supply the blood component storage solution to the blood treating filter 8, and is provided, at the base end of the tube 14, with a supply control member 14*a* for controlling the supply of the blood component storage solution to the blood treating filter 8. The supply control member 14*a* is a flow path plugging member the breakage of which causes opening of a flow path (starts the supply of the blood component storage solution) like the above-mentioned flow path plugging member 15*a*, or a connection needle with which the storage solution supply means (bag-shaped container) 7 is punctured to thereby start the supply of the blood component storage solution, or the like.

Besides, while the storage solution supply means 7 is preliminarily connected to the blood treating filter 8 through the tube 14 and the tube 15 in FIG. 1, a configuration may be adopted in which the storage solution supply means 7 and the blood treating filter 8 are interconnected by connecting the tube 14 and the tube 15 to each other through the use of a commercial sterile connection device at the time of using the blood bag system 30, in other words, at the time of supplying the blood component storage solution into the blood treating filter 8.

The blood component storage solution is a solution for recovering the blood remaining in the blood treating filter 8 and for preventing the function of the blood component not removed in the blood treating filter 8 (the filter section 8*d*) from being lowered, and, in the blood bag system 30, it is preferably a red blood cell storage solution. As the red blood cell storage solution, there may be used OPTISOL (registered trademark), MAP, SAGM, ADSOL or the like. The amount of the blood component storage solution is preferably 50 to 200 ml. If the amount is less than 50 ml, the recovery factor of the blood component remaining in the blood treating filter 8 would be more liable to be lowered, and a lowering in the function of a blood component preparation or preparations (specifically, CRC) prepared in the blood bag system 30 would be more liable to occur. On the other hand, if the solution amount exceeds 200 ml, economy would be liable to be lowered.

(Second Bag)

The second bag 2, which is for containing a treated blood obtained by treatment of the blood supplied from the first bag 1 by the blood treating filter 8, is a bag-shaped container being the same as or similar to the first bag 1 in material and shape. Here, the treated blood is specifically a blood deprived of white blood cells and platelets. In addition, the second bag 2 is connected with the tube 16 for supplying the treated blood from the blood treating filter 8 (the outflow port 8*b*) into the second bag 2, and with the tube 18 through which part (specifically, PPP) of the blood component or components (specifically, PPP and CRC) separated from the treated blood is transferred into the fourth bag 4 described later. Incidentally, the tube 16 is provided with a tube clamp 22, while the tube 18 is provided with a flow path plugging member 18*a*. The flow path plugging member 18*a* is the same as or similar to the above-mentioned flow path plugging member 15*a*, the breakage of which causes opening of a flow path. In addition, the internal volume of the second bag is preferably 200 to 1000 ml.

(Third Bag)

The third bag 3, for temporarily containing a recovered blood which is recovered by replacement of the blood remaining inside the blood treating filter 8 after treatment of a blood in the blood treating filter 8 by the blood component storage solution, is a bag-shaped container being the same as or similar to the first bag 1 in material and shape; preferably, the third bag 3 is a bag-shaped container formed from polycarbonate sheets or the like higher in strength than the polyvinyl chloride sheets or the like constituting the first bag 1. Besides, the third bag 3 is connected with the tube 17 for supplying the inside thereof with the recovered blood from the blood treating filter 8 (the outflow port 8*b*). Incidentally, the tube 17 is provided with a tube clamp 17*a*. In addition, the internal volume of the third bag 3 is preferably 50 to 200 ml.

(Fourth Bag)

The fourth bag 4, into which the blood component (specifically, PPP) separated from the treated blood and contained in the second bag 2 is transferred and in which the transferred blood component (specifically, PPP) is contained, is a bag-shaped container being the same as or similar to the first bag 1 in material and shape. In addition, the fourth bag 4 is connected with the tube 18 for supplying the inside thereof with the blood component (specifically, PPP) separated from the second bag 2. Besides, the internal volume of the fourth bag 4 is preferably 200 to 1000 ml.

In addition, in the blood bag system 30, the blood collecting tube 11 and the tubes 14, 15, 16, 17 and 18 are each formed from a flexible resin such as polyvinyl chloride.

Incidentally, in the blood bag system 30, preferably, the blood treating filter 8 is a white blood cell and platelet removing filter, the first bag 1 is a blood collecting bag for containing whole blood, the second bag 2 is a red blood cell storing bag, and the fourth bag 4 is a plasma storing bag. Besides, the blood component storage solution is preferably a red blood cell storage solution.

Now, the second embodiment of the blood bag system will be described below.

As shown in FIG. 2, a blood bag system 31 has the first bag 1 and the storage solution supply means 7 on the upstream side of the blood treating filter 8, and has the second bag 2, the third bag 3, the fourth bag 4, a fifth bag 5 and a sixth bag 6 on the downstream side of the blood treating filter 8.

In the blood bag system 31, the first bag 1 is connected to the inflow port 8a of the blood treating filter 8 through the tube 15, and the storage solution supply means 7 is connected to the inflow port 8a of the blood treating filter 8 through the tube 14 branched from the tube 15. In addition, the second bag 2 is connected to the outflow port 8b of the blood treating filter 8 through the tube 16; the third bag 3 is connected to the outflow port 8b of the blood treating filter 8 through the tube 17 branched from the tube 16; the fourth bag 4 is connected to the second bag through the tube 18; the fifth bag 5 is connected to the third bag 3 and the fourth bag 4 through tubes 19 and 21; and the sixth bag 6 is connected to the second bag 2 and the fourth bag 4 through a tube 20 branched from the tube 18. Now, configurations of these members will be described below.

(Blood Treating Filter)

The blood treating filter 8 is the same as or similar to that in the above-described blood bag system 30 in configuration, but it is preferably a filter for performing a treatment of removing only white blood cells. The filter section 8d of such the blood treating filter 8 preferably has a surface zeta potential of −2.0 to +2.0 mV, more preferably +0.5 to +1.0 mV.

(First Bag)

The first bag 1 is the same as or similar to that in the above-described blood bag system 30, and, therefore, description thereof is omitted. Incidentally, the treated blood is preferably a blood from which only while blood cells have been removed.

(Storage Solution Supply Means)

The storage solution supply means 7 is the same as or similar to that in the above-mentioned blood bag system 30 in configuration, with the blood component storage solution being preferably a platelet storage solution. As the platelet storage solution, there may be used Composol, T-sol, Intersol, Plasma LiteA, SSP, SSP+, Seto solution, M-sol or the like.

(Second Bag, Third Bag and Fourth Bag)

The second bag 2, the third bag 3 and the fourth bag 4 are the same as or similar to those in the above-described blood bag system 30, and, therefore, descriptions thereof are omitted. Incidentally, the blood components separated in the second bag 2 are preferably PRP and CRC, the blood component transferred into the fourth bag 4 is preferably PRP, and the PRP is preferably separated into PPP and PC. In addition, to the third bag 3, the fifth bag 5 into which to transfer the blood component separated in the third bag 3 is connected through the tube 19. Besides, the fourth bag 4 and the fifth bag 5 are interconnected through the tube 21 through which to transfer the blood component in the fifth bag 5 to the fourth bag 4. In addition, the tube 19 is provided with a flow path plugging member 19a on the third bag 3 side, and the tube 21 is provided with a flow path plugging member 21a on the fourth bag 4 side. The flow path plugging member 19a and the flow path plugging member 21a are each the same as or similar to the above-mentioned flow path plugging member 15a, the breakage of which causes opening of a flow path.

(Fifth Bag)

The fifth bag 5, to which the blood component (specifically, the blood component storage solution and PC) separated from the recovered blood contained in the third bag 3 are transferred and in which the transferred blood component (specifically, the blood component storage solution and PC) are temporarily contained, is a bag-shaped container being the same as or similar to the third bag 3 in material and shape. In addition, the fifth bag 5 is connected with the tube 19 for supplying the inside thereof with the blood component (specifically, the blood storage solution and PC) separated in the third bag 3, and is connected with the tube 21 for transferring the thus supplied blood component into the fourth bag 4. Besides, the internal volume of the fifth bag 5 is preferably 50 to 200 ml. Incidentally, the fifth bag 5 may be a bag 9 united with the third bag 3 through a diaphragm 9a (see FIG. 4).

(Sixth Bag)

The sixth bag 6, to which the blood component (specifically, PPP) separated from the blood component (specifically, PRP) transferred into the fourth bag 4 is transferred and in which the thus transferred blood component (specifically, PPP) is contained, is a bag-shaped container being the same as or similar to the first bag 1 in material and shape. In addition, the sixth bag 6 preferably contains a red blood cell storage solution before the blood component is contained thereinto. As the red blood storage solution, there may be used OPTISOL, MAP, SAGM, ADSOL or the like. Besides, the sixth bag 6 is connected with the tube 20 branched from the tube 18, for supplying the inside thereof with the blood component (specifically, PPP) separated in the fourth bag 4 and for supplying the blood component storage solution to the blood component (CRC) separated in the second bag 2. At the base end of the tube 20 is provided a flow path plugging member 20a (the same as or similar to the above-mentioned flow path plugging member 15a), the breakage of which causes opening of a flow path.

Besides, in the blood bag system 31, the blood collecting tube 11 and the tubes 14, 15, 16, 17, 18, 19, and 21 are each formed from a flexible resin such as polyvinyl chloride. In addition, the tube 16 is preferably provided with the tube clamp 22, in the same manner as in the above-described blood bag system 30. Besides, the tube 18 is preferably provided with a tube clamp 23, so as to prevent the blood component (PRP) transferred into the fourth bag 4 from flowing back toward the side of the second bag (the bag in which CRC is contained) 2.

Incidentally, in the blood bag system 31, preferably, the blood treating filter 8 is a white blood cell removing filter, the first bag 1 is a blood collecting bag in which to contain whole blood, the second bag 2 is a red blood cell storing bag, the fourth bag 4 is a platelet storing bag, and the sixth bag 6 is a plasma storing bag. In addition, the blood component storage solution is preferably a platelet storage solution.

The second embodiment of the blood bag system according to the present invention may be a blood bag system 32 shown in FIG. 3. The blood bag system 32 is different from the above-described blood bag system 31 in layout of the second to sixth bags, but is the same as or similar to the blood bag system 31 in configuration; therefore, the description thereof is omitted.

<Blood Treating Method>

Figure 5:
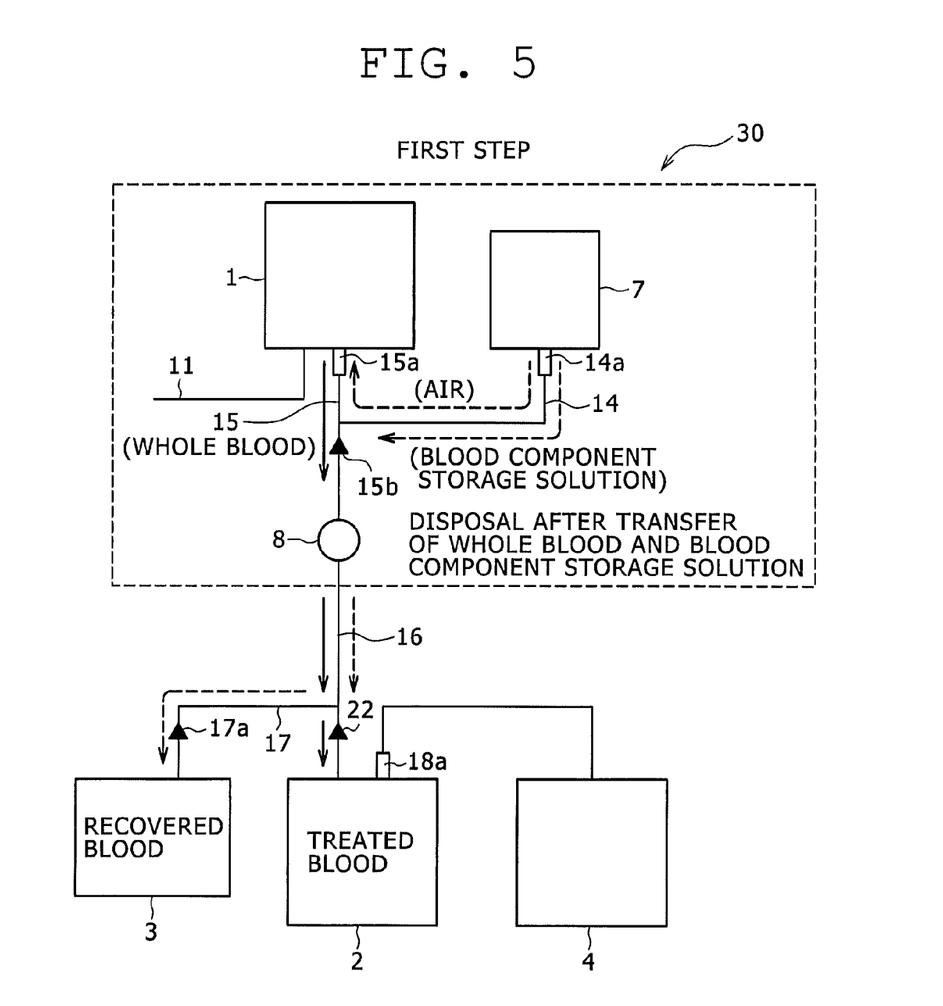
FIG. 5 schematically shows the procedure of a first step in a first embodiment of a blood treating method according to the present invention.
Figure 6:
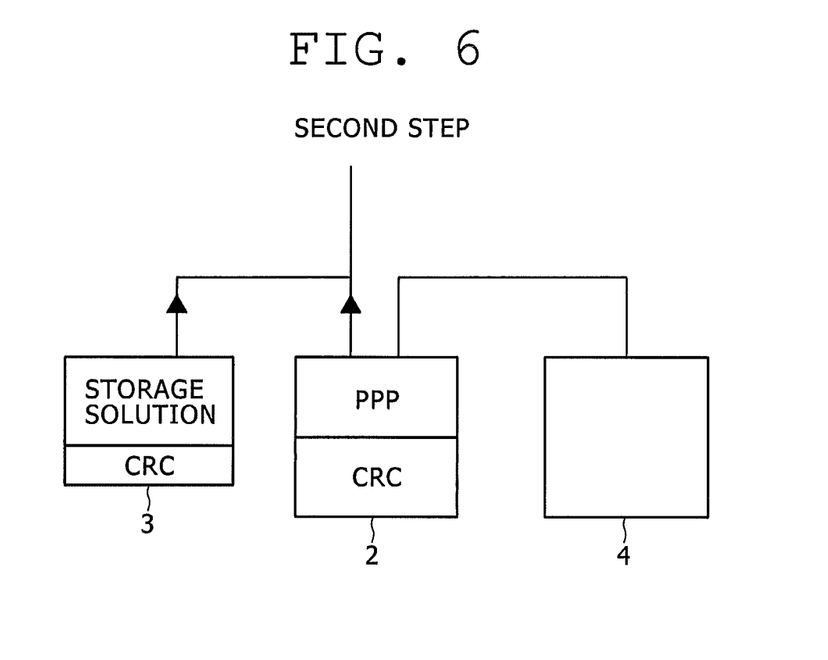
FIG. 6 schematically shows the procedure of a second step in the first embodiment of the blood treating method according to the present invention.
Figure 7:
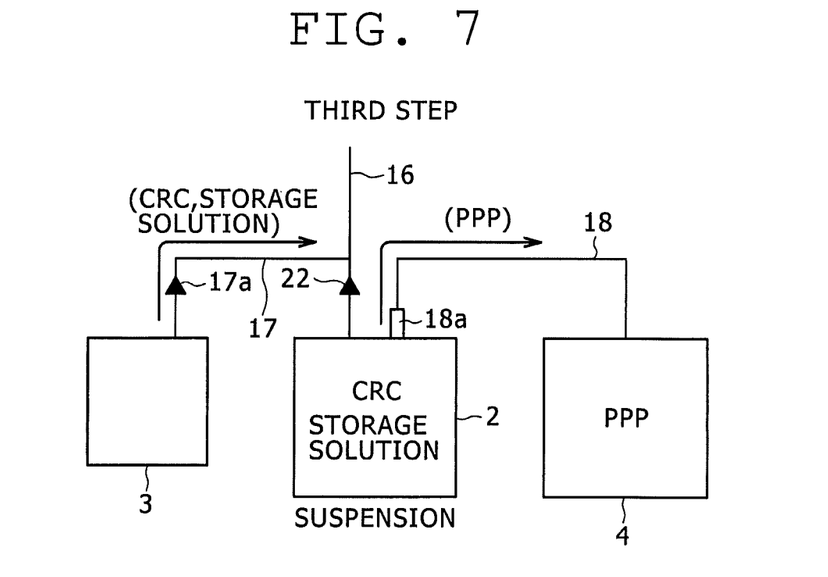
FIG. 7 schematically shows the procedure of a third step in the first embodiment of the blood treating method according to the present invention.

The blood treating method according to the present invention will be described referring to the drawings. FIGS. 5 to 7 schematically show the procedure in the first embodiment of the blood treating method, and FIGS. 8 to 12 schematically show the procedure in the second embodiment of the blood treating method. Besides, as for the configuration of the blood bag system, description will be made referring to FIG. 1 or 2, as required.

The first embodiment of the blood treating method is a method of treating a blood by use of the blood bag system 30 (see FIG. 1) according to the above-described first embodiment, the method including first to third steps. Now, each of the steps will be described below (see FIGS. 5 to 7).

Incidentally, in the first embodiment of the blood treating method, the following operation (an operation for containing a blood into the first bag 1) is conducted before carrying out the first step. Specifically, the blood collecting needle 10 shown in FIG. 1 is made to puncture a donor to start blood collection. If necessary, an initial-flow blood is collected into the initial-flow blood collecting implement (testing blood bag) 12, and a predetermined amount of blood is contained into the first bag 1 through the blood collecting tube 11. Thereafter, a portion, on the blood collecting needle 10 side, of the blood collecting tube 11 is cut by fusion, and the part on the blood collecting needle 10 side is separated from the blood bag system 30. Thereafter, the first to third steps are carried out.

(First Step)

As shown in FIG. 5, the flow path plugging member 15*a* in the tube 15 connected to the first bag 1 is broken, to open the flow path. Next, the blood contained in the first bag 1 is supplied into the blood treating filter 8 through the tube 15, and the blood is treated by the blood treating filter 8, to be contained through the tube 16 into the second bag 2 as a treated blood.

Thereafter, the tube clamp 22 is closed, to close the flow path on the second bag 2 side of the tube 16. Next, the supply control member 14*a* in the tube 14 connected to the storage solution supply means 7 is controlled, whereby the blood component storage solution (specifically, a red blood cell storage solution) is supplied from the storage solution supply means 7 into the blood treating filter 8 through the tube 14. Then, the blood remaining inside the blood treating filter 8 is replaced by the blood component storage solution, whereby the remaining blood is recovered through the tubes 16 and 17, to be contained into the third bag 3 as a recovered blood.

Then, after the tube clamp 17*a* is closed, the tube 16 is cut through fusion by use of a tube sealer, and the first bag 1 and the storage solution supply means 7 as well as the blood treating filter 8 are separated from the blood bag system 30, to be disposed of.

Incidentally, it is preferable that before the blood component storage solution is supplied into the blood treating filter 8, the tube clamp 15*b* is closed and the blood component solution is supplied from the storage solution supply means 7 into the first bag 1, so as to discharge the air present in the tube 14 into the first bag 1 emptied upon supply of the blood therefrom. This ensures that the amount of air supplied into the blood treating filter 8 is extremely small, so that the recovery of the blood remaining in the blood treating filter 8 by the blood component storage solution would not be hampered by air block. Consequently, recovery factor of the remaining blood is enhanced.

(Second Step)

As shown in FIG. 6, the second bag 2 is centrifuged, whereby the treated blood contained in the second bag 2 is separated into two blood components (upper and lower two layers). Here, the centrifugation condition is preferably strong centrifugation (3600 to 5500 G)×(6 to 8 min). Specifically, the treated blood is separated into PPP (upper layer) and CRC (lower layer) in the second bag 2. In this instance, the third bag 3 is centrifuged together with the second bag 2, so that the recovered blood is separated into the blood component storage solution (storage solution) and CRC in the third bag 3.

(Third Step)

As shown in FIG. 7, the flow path plugging member 18*a* in the tube 18 is broken to open the flow path, and then, in the manner of leaving one of the blood components (the lower layer, specifically, CRC) in the second bag 2, the other blood component (the upper layer, specifically, PPP) is transferred through the tube 18 into the fourth bag 4. Then, the tube 18 is cut through fusion by use of a tube sealer, to separate off the fourth bag 4. Thereafter, the tube clamp 17*a* on the tube 17 and the tube clamp 22 on the tube 16 are opened, to open the flow path on the second bag 2 side of the tube 16, and the recovered blood (specifically, the storage solution and CRC) in the third bag 3 is transferred through the tubes 16 and 17, to be mixed with the one blood component (specifically, CRC) remaining in the second bag 2. Then, the tube 17 is cut through fusion by use of a tube sealer, to separate off the second bag 2. As a result, CRC suspended in the storage solution (specifically, the red blood cell storage solution) is prepared in the second bag 2, and PPP is prepared in the fourth bag.

In the next place, the second embodiment of the blood treating method is a method of treating a blood by use of the above-described blood bag system 31 (see FIG. 2), the method including first to fifth steps. Besides, in a blood treating method using the blood bag system 32 (see FIG. 3), also, a blood is treated by the same or similar steps. Now, each of the steps of the blood treating method will be described below, taking the case of using the blood bag system 31 (see FIG. 2) as an example (see FIGS. 8 to 12).

Incidentally, in the second embodiment of the blood treating method, also, like in the above-described first embodiment, the operation of containing a blood into the first bag 1 is conducted before carrying out the first step.

(First Step)

Figure 8:
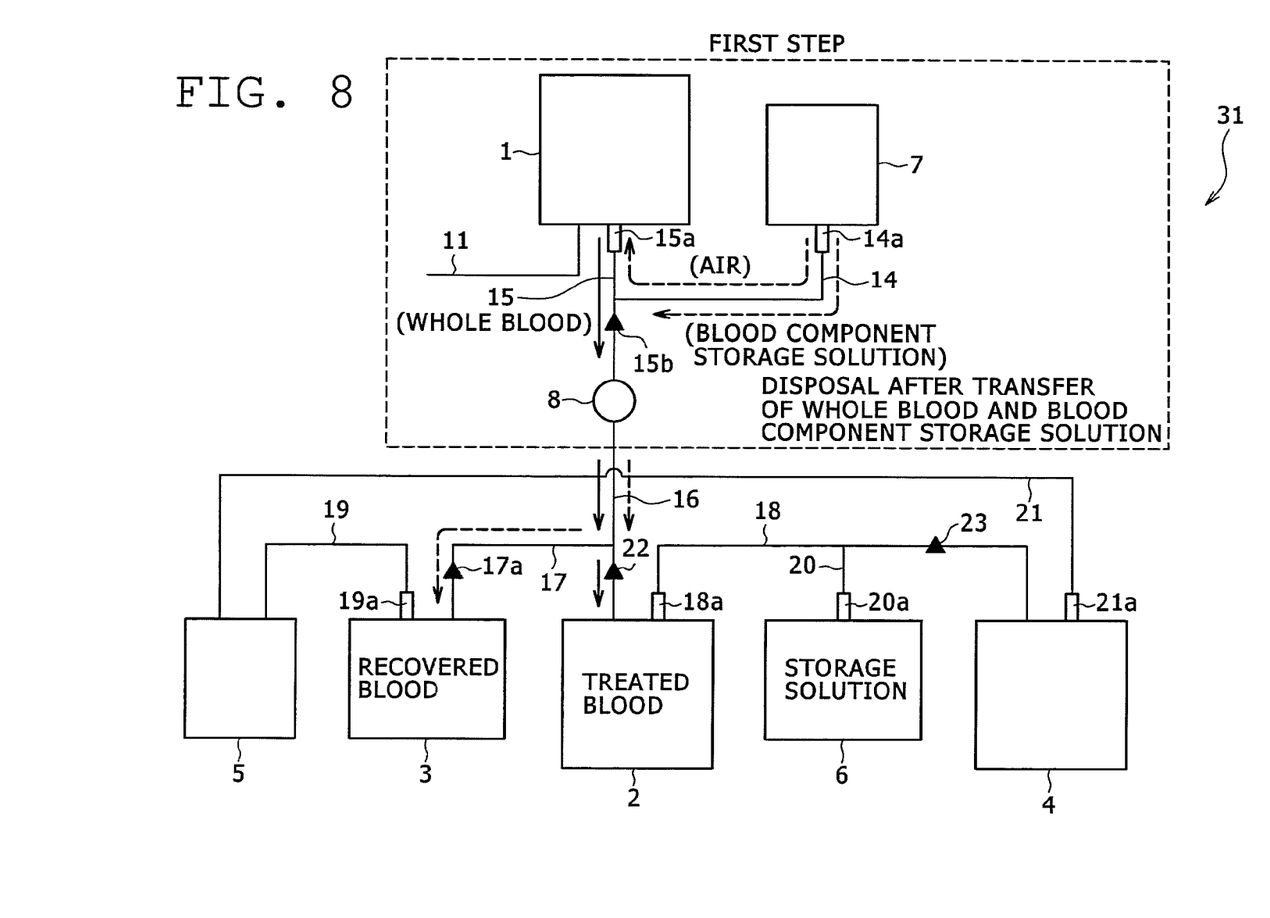
FIG. 8 schematically shows the procedure of a first step in a second embodiment of the blood treating method according to the present invention.

As shown in FIG. 8, like in the blood treating method (the first step, see FIG. 5) according to the above-described first embodiment, the blood contained in the first bag 1 is treated by the blood treating filter 8, to be contained into the second bag 2 as a treated blood. Thereafter, the blood component storage solution (specifically, a platelet storage solution) is supplied from the storage solution supply means 7 into the blood treating filter 8, whereby the blood remaining in the blood treating filter 8 is replaced by the blood component storage solution, and the blood is transferred to and contained in the third bag 3 as a recovered blood.

(Second Step)

Figure 9:
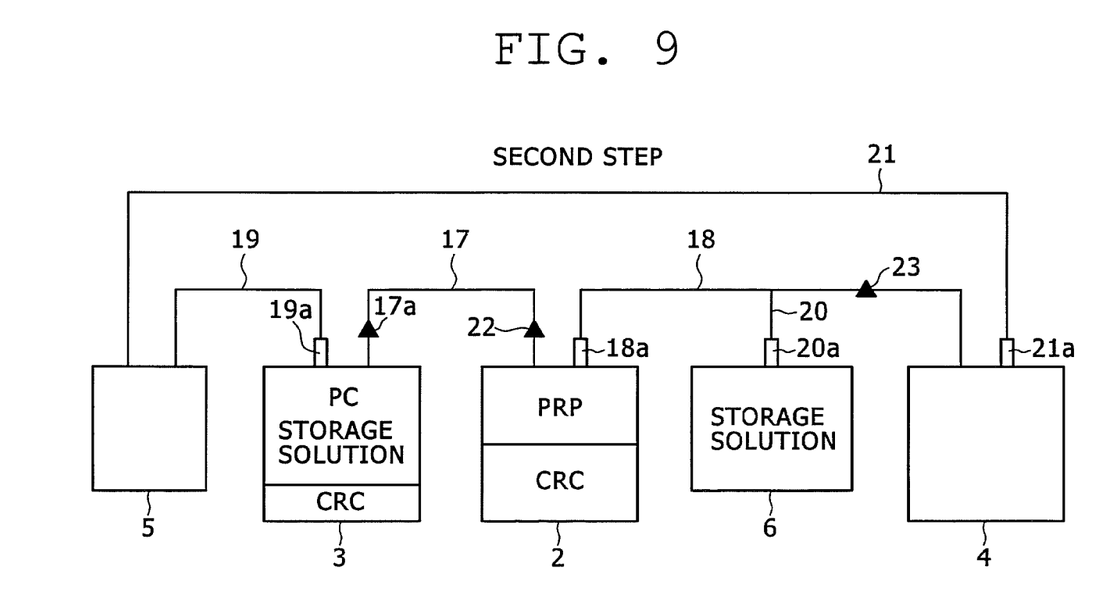
FIG. 9 schematically shows the procedure of a second step in the second embodiment of the blood treating method according to the present invention.

As shown in FIG. 9, the second bag 2 and the third bag 3 are centrifuged, whereby the treated blood contained in the second bag 2 and the recovered blood contained in the third bag 3 are each separated into two blood components (upper and lower two layers). Here, the centrifugation condition is preferably weak centrifugation (600 to 1500 G)×(3 to 8 min). Specifically, the treated blood is separated into PRP (upper layer) and CRC (lower layer) in the second bag 2, and the recovered blood is separated into the blood component storage solution (storage solution) and PC (upper layer) and CRC (lower layer) in the third bag 3.

(Third Step)

Figure 10:
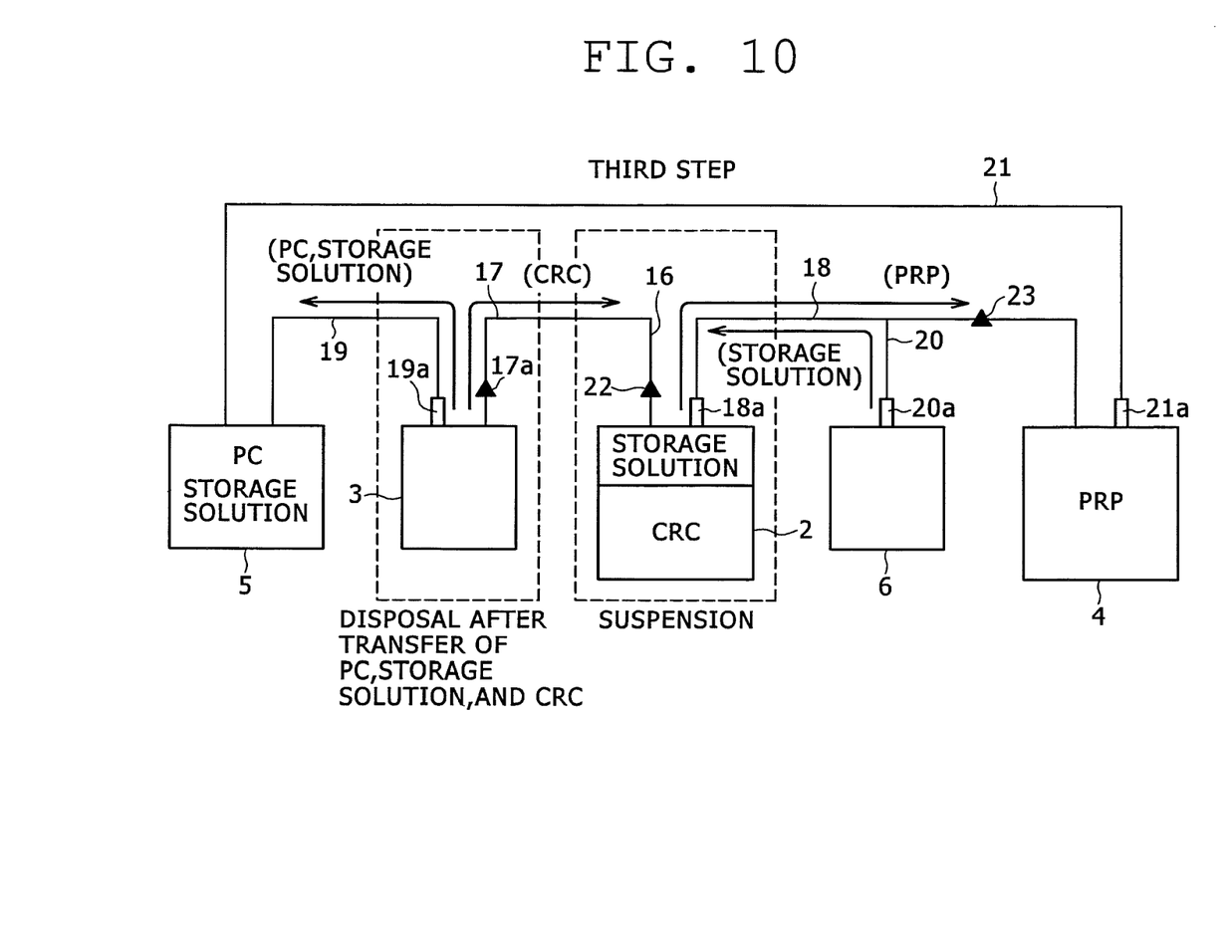
FIG. 10 schematically shows the procedure of a third step in the second embodiment of the blood treating method according to the present invention.

As shown in FIG. 10, the flow path plugging member 18*a* in the tube 18 is broken to open the flow path, and the tube clamp 23 is opened so that, in such a manner as to leave one of the blood components (the lower layer, specifically CRC) in the second bag 2, the other blood component (the upper layer, specifically, PRP) is transferred through the tube 18 into the fourth bag 4. In addition, the flow path plugging member 19*a* in the tube 19 is broken to open the flow path, and, in the manner of leaving one of the blood components (the lower layer, specifically, CRC) in the third bag 3, the other blood component (the upper layer, specifically, PC and the storage solution) is transferred into the fifth bag 5. Next, the tube 19 is cut by fusion, to separate the fifth bag 5 from the third bag 3. Thereafter, the tube clamp 22 on the tube 16 and the tube clamp 17*a* on the tube 17 are opened, to open the flow path on the second bag 2 side of the tube 16, and the one blood component (the lower layer, specifically, CRC) remaining in the third bag 3 is transferred through the tubes 16 and 17 to the second bag 2, to be mixed with the one blood component (the lower layer, specifically, CRC) remaining in the second bag 2. In this instance, the tube clamp 23 on the tube 18 is closed so as to prevent the other blood component (specifically, PRP) in the fourth bag 4 from flowing back toward the side of the second bag 2. As a result, CRC is prepared in the second bag 2.

Besides, in the case where a red blood cell storage solution (storage solution) is preliminarily contained in the sixth bag 6, the flow path plugging member 20a in the tube 20 is broken to open the flow path, and the storage solution contained in the sixth bag 6 is transferred through the tubes 18 and 20 into the second bag 2. Consequently, CRC suspended in the storage solution (specifically, the red blood cell storage solution) is prepared in the second bag 2.

Then, the tubes 16, 17 and 18 are cut by fusion, to separate the second bag 2 from the third bag 3 and the sixth bag 6.

(Fourth Step)

Figure 11:
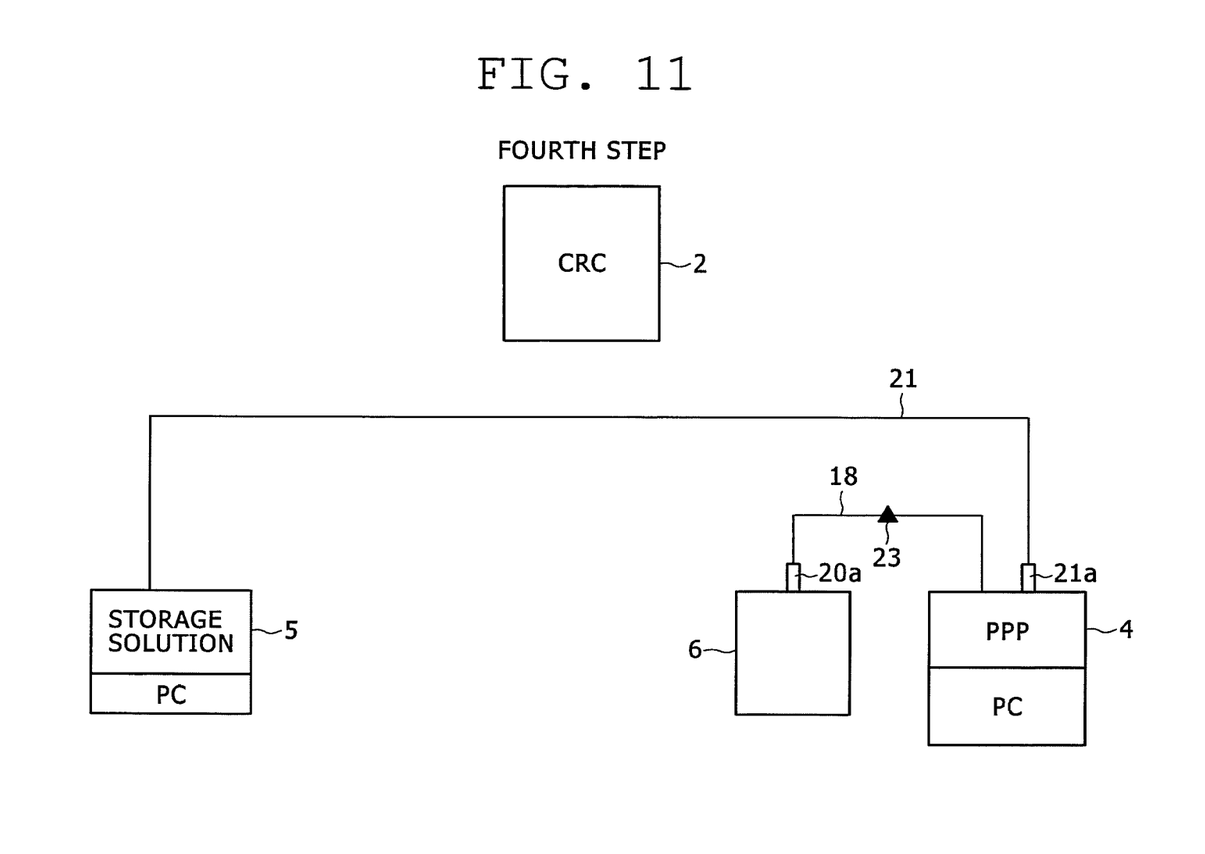
FIG. 11 schematically shows the procedure of a fourth step in the second embodiment of the blood treating method according to the present invention.

As shown in FIG. 11, the fourth bag 4 is centrifuged, whereby the other blood component (specifically, PRP) contained in the bag is separated into two blood components (upper and lower two layers). Here, the centrifugation condition is preferably strong centrifugation (3600 to 5500 G)×(6 to 8 min). Specifically, the other blood component (specifically, PRP) is separated into PPP (upper layer) and PC (lower layer) in the fourth bag 4. In this case, the fifth bag 5 is centrifuged together with the fourth bag 4, so that the other blood component is separated into the storage solution (specifically, the platelet storage solution) and PC in the fifth bag 5.

(Fifth Step)

Figure 12:
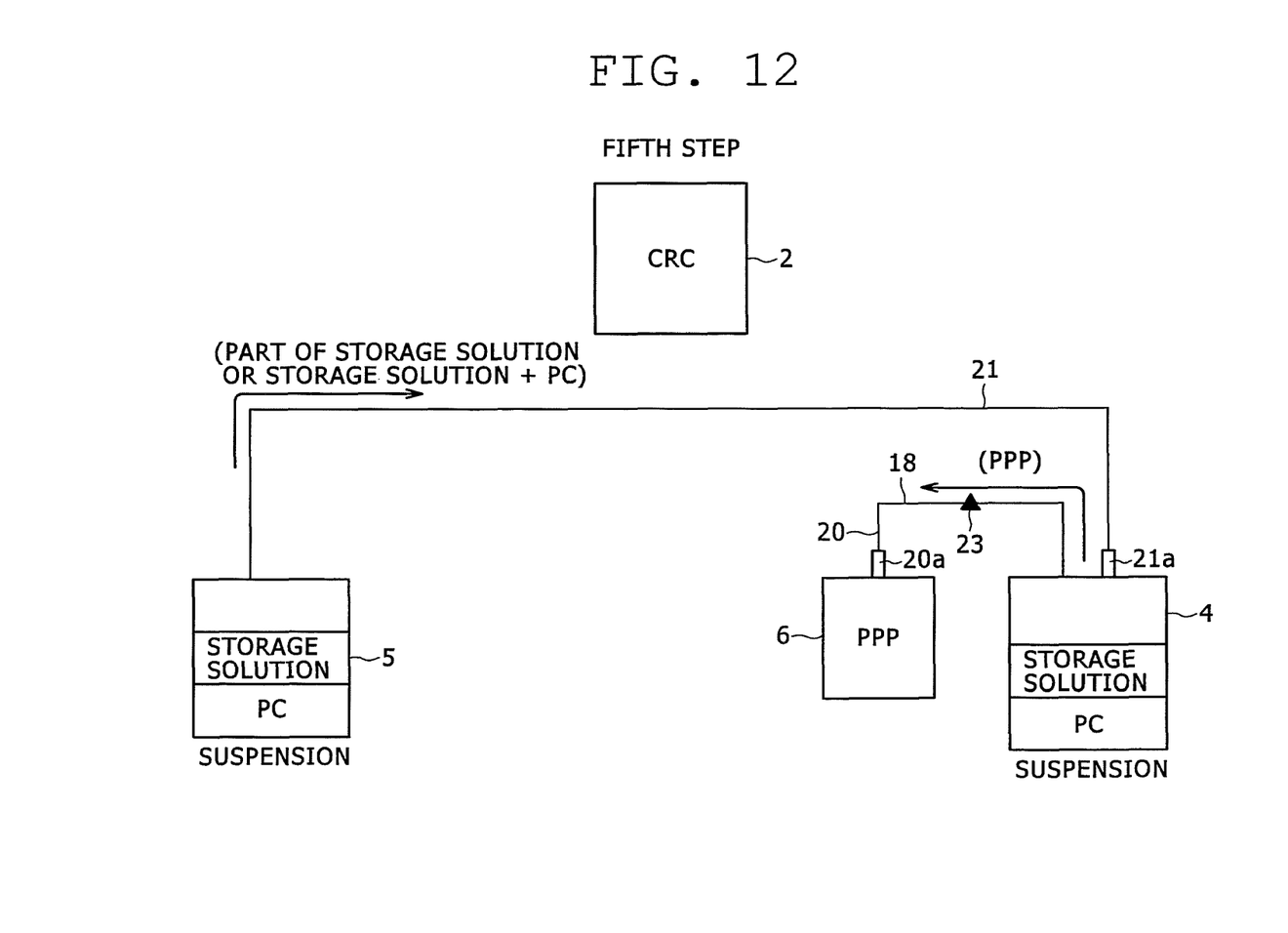
FIG. 12 schematically shows the procedure of a fifth step in the second embodiment of the blood treating method according to the present invention.

As shown in FIG. 12, the tube clamp 23 on the tube 18 is opened, to open the flow path of the tube 18. Then, in such a manner as to leave one of the blood components (the lower layer, PC) in the fourth bag 4, the other blood component (the upper layer, PPP) is transferred through the tubes 18 and 20 into the sixth bag 6, which is empty. Next, the tube 20 is cut by fusion, to separate the sixth bag 6 from the fourth bag 4. Thereafter, the flow path plugging member 21a in the tube 21 is broken to open the flow path, and then the other blood component (the storage solution and PC) in the fifth bag 5 is transferred through the tube 21 to the fourth bag 4, to be mixed with the one blood component (the lower layer, PC) remaining in the fourth bag 4. Subsequently, the tube 21 is cut by fusion, to separate the fifth bag 5 from the fourth bag 4. As a result, PPP is prepared in the sixth bag 6, PC suspended in the storage solution (specifically, the platelet storage solution) is prepared in the fourth bag 4. Incidentally, part of the storage solution separated in the fifth bag 5 may be transferred to and mixed with the PC prepared in the fourth bag 4 so that PC suspended in the storage solution is conditioned in both the fourth bag 4 and the fifth bag 5.

In addition, the second embodiment of the blood treating method may be carried out in such a manner that in the third step, only the operations of transferring the other blood component (the upper layer, specifically, PRP) in the second bag 2 shown in FIG. 10 into the fourth bag 4 and transferring the other blood component (the upper layer, specifically, the platelet storage solution and PC) in the third bag 3 into the fifth bag 5 are conducted, and either the operation by which the one blood component (the lower layer, specifically, CRC) left in the third bag 3 shown in FIG. 10 is transferred to and mixed with the one blood component (the lower layer, specifically, CRC) left in the second bag 2, or this operation and the operation by which the red blood cell storage solution contained in the sixth bag 6 is transferred to and mixed with the one blood component (the lower layer, specifically, CRC) left in the second bag 2, are carried out as a sixth step after completion of the fifth step.

EXPLANATION OF REFERENCE

1 First bag
2 Second bag
3 Third bag
4 Fourth bag
5 Fifth bag
6 Sixth bag
7 Storage solution supply means
8 Blood treating filter
30, 31, 32 Blood bag system

The invention claimed is:

1. A blood bag system comprising:
    a blood treating filter for treating a blood;
    a first bag for containing therein a blood to be supplied to the blood treating filter;
    a second bag for containing therein the blood treated by the blood treating filter;
    storage solution supply means for supplying a blood component storage solution to the blood treating filter;
    a third bag into which a blood remaining in the blood treating filter replaced by the blood component storage solution is transferred and in which the recovered blood is temporarily contained;
    a fourth bag into which a blood component separated from the treated blood contained in the second bag is transferred and in which the thus transferred blood component is contained;
    a fifth bag into which a blood component separated from the recovered blood contained in the third bag is transferred and in which the thus transferred blood component is temporarily contained; and
    a sixth bag into which a blood component separated further from the blood component transferred into the fourth bag is transferred and in which the thus transferred blood component is temporarily contained.

2. The blood bag system according to claim 1,
    wherein the blood treating filter is a white blood cell and platelet removing filter for removing white blood cells and platelets from whole blood,
    the first bag is a blood collecting bag for collecting whole blood,
    the second bag is a red blood cell storing bag,
    the blood component storage solution is a red blood cell storage solution, and
    the fourth bag is a plasma storing bag.

3. The blood bag system according to claim 1,
    wherein the blood treating filter is a white blood cell removing filter for removing white blood cells from whole blood,
    the first bag is a blood collecting bag for collecting whole blood,
    the second bag is a red blood cell storing bag,
    the blood component storage solution is a platelet storage solution,
    the fourth bag is a platelet storing bag, and
    the sixth bag is a plasma storing bag.

4. The blood bag system according to claim 3, wherein the sixth bag contains a red blood cell storage solution therein before containing the blood component.

5. The blood bag system according to claim 1, wherein the third bag and the fifth bag are united together through a diaphragm.

6. The blood bag system according to claim 1, wherein the storage solution supply means is a bag-shaped container containing the blood component storage solution therein which container is preliminarily connected, or the bag-shaped container which is connected in a sterile manner before use.

7. A method for treating a blood by use of the blood bag system comprising:
- a blood treating filter for treating a blood;
- a first bag for containing therein a blood to be supplied to the blood treating filter;
- a second bag for containing therein the blood treated by the blood treating filter;
- storage solution supply means for supplying a blood component storage solution to the blood treating filter;
- a third bag into which a blood remaining in the blood treating filter replaced by the blood component storage solution is transferred and in which the recovered blood is temporarily contained;
- a fourth bag into which a blood component separated from the treated blood contained in the second bag is transferred and in which the thus transferred blood component is contained, the method comprising:
- a first step of supplying the blood contained in the first bag into the blood treating filter, containing the blood treated by the blood treating filter into the second bag, thereafter supplying the blood component storage solution from the storage solution supply means into the blood treating filter so as to recover the blood remaining in the blood treating filter, and containing the recovered blood into the third bag;
- a second step of centrifuging the second bag so as to separate the treated blood contained in the second bag into two blood components; and
- a third step of transferring, in such a manner as to leave one of the blood components in the second bag, the other blood component to the fourth bag, and thereafter transferring the recovered blood contained in the third bag to the second bag so as to mix the recovered blood with the one blood component.

8. A method of treating a blood by use of the blood bag system comprising:
- a blood treating filter for treating a blood;
- a first bag for containing therein a blood to be supplied to the blood treating filter;
- a second bag for containing therein the blood treated by the blood treating filter;
- storage solution supply means for supplying a blood component storage solution to the blood treating filter;
- a third bag into which a blood remaining in the blood treating filter replaced by the blood component storage solution is transferred and in which the recovered blood is temporarily contained;
- a fourth bag into which a blood component separated from the treated blood contained in the second bag is transferred and in which the thus transferred blood component is contained;
- a fifth bag into which a blood component separated from the recovered blood contained in the third bag is transferred and in which the thus transferred blood component is temporarily contained; and
- a sixth bag into which a blood component separated further from the blood component transferred into the fourth bag is transferred and in which the thus transferred blood component is temporarily contained, the method comprising:
- a first step of supplying the blood contained in the first bag into the blood treating filter, containing the blood treated by the blood treating filter into the second bag, thereafter supplying the blood component storage solution from the storage solution supply means into the blood treating filter so as to recover the blood remaining in the blood treating filter, and containing the recovered blood into the third bag;
- a second step of centrifuging the second bag and the third bag so as to separate each of the treated blood contained in the second bag and the recovered blood contained in the third bag into two blood components;
- a third step of transferring, in such a manner as to leave one of the blood components in the second bag, the other blood component to the fourth bag, and transferring, in such a manner as to leave one of the blood components in the third bag, the other blood component to the fifth bag, followed by transferring the one blood component in the third bag to the second bag so as to mix the thus transferred one blood component with the one blood component in the second bag;
- a fourth step of centrifuging the fourth bag so as to further separate the other blood component contained in the fourth bag into two blood components; and
- a fifth step of transferring, in such a manner as to leave one of the blood components in the fourth bag, the other blood component to the sixth bag, and thereafter transferring the other blood component in the fifth bag to the fourth bag so as to mix the thus transferred other blood component with the one blood component in the fourth bag.

* * * * *